US00PP31230P3

(12) United States Plant Patent
Kunieda

(10) Patent No.: US PP31,230 P3
(45) Date of Patent: Dec. 17, 2019

(54) ***ROSA* L. PLANT NAMED '80100WABARA-CP'**

(50) Latin Name: ***Rosa* L.**
Varietal Denomination: 80100WABARA-CP

(71) Applicant: Rose Universe Co., Ltd., Shiga (JP)

(72) Inventor: Keiji Kunieda, Shiga (JP)

(73) Assignee: Rose Universe Co., Ltd., Shiga (JP)

( * ) Notice: Subject to any disclaimer, the term of this patent is extended or adjusted under 35 U.S.C. 154(b) by 0 days.

(21) Appl. No.: 15/932,568

(22) Filed: Mar. 15, 2018

(65) Prior Publication Data

US 2019/0239401 P1 Aug. 1, 2019

(30) Foreign Application Priority Data

Jan. 30, 2018 (JP) ..... PBR 32825

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./102, 104
CPC ..... A01H 5/02; A01H 6/749
See application file for complete search history.

*Primary Examiner* — Keith O. Robinson
(74) *Attorney, Agent, or Firm* — Kilpatrick Townsend & Stockton LLP

(57) ABSTRACT

Described herein is a new and distinct rose plant named '80100WABARA-CP' that has large, rounded, yellow and brown blend flowers with dense petals. The variety is primarily used as a potted plant and for cut flowers.

4 Drawing Sheets

Genus and species: The rose variety of this invention is botanically identified as *Rosa* L.

Variety denomination: The variety denomination is '80100WABARA-CP'.

CROSS-REFERENCES TO RELATED APPLICATIONS

This application claims priority to Japanese Plant Variety Protection Application No. 32825, filed Jan. 30, 2018.

BACKGROUND OF THE INVENTION

The present invention is a new and distinct variety of a *Rosa* L. rose plant that was obtained from a cross between maternal variety 'An' (unpatented) and an unnamed paternal variety of unknown parentage owned by the breeder. The cross was performed by hand pollination in May 2014 and seeds planted in January 2015. '80100WABARA-CP' was selected from the varieties that flowered in September 2017. Stable characteristics were confirmed following selection. The plant was asexually reproduced by grafting.

BRIEF SUMMARY OF THE INVENTION

'80100WABARA-CP' is reproduced by grafting. '80100WABARA-CP' can be distinguished from the maternal variety 'An' by: (1) a larger number of petals (80 petals compared to 54 for 'An'); (2) color grouping (yellow and brown mix compared to pink blend for 'An'); (3) petal shape (ellipitic center part, obcordate outside compared to obovate for 'An'); (4) main color of the inner side of the petal (RHS 8D compared to RHS 49C for 'An'); petal secondary color (RHS 4C compared to absent for 'An'). '80100WABARA-CP' is also distinguished from comparison variety 'Rikuhotaru' (unpatented) by its fragrance, which is medium compared to strong for 'Rikuhotaru'; and the main color of the inner side of the petal, which is RHS 8D for '80100WABARA-CP' and RHS 13D for 'Rikuhotaru'.

The variety '80100WABARA-CP' is maintained at Shiga-ken Moryama-shi, 1465 Sugie-cho, Japan and is maintained by soil cultivation. The variety is primarily used as a potted plant and for cut flowers. Planting in Japan is from mid-October to late December. Grafting is from late September to early October. The plant will flower annually when grown in a greenhouse. The plant can be grown at a temperature of 5° C. to 40° C.

BRIEF DESCRIPTION OF THE PHOTOGRAPHS

The accompanying photographs illustrate the appearance of the new *Rosa* L. variety '80100WABARA-CP'. The plant depicted in the photographs is about two years in age. The colors in the photographs are depicted as nearly true as is reasonably possible to obtain in colored reproductions of this type. Colors as shown in the photographs may differ slightly from the color values cited in the detailed botanical description.

Figure 1:
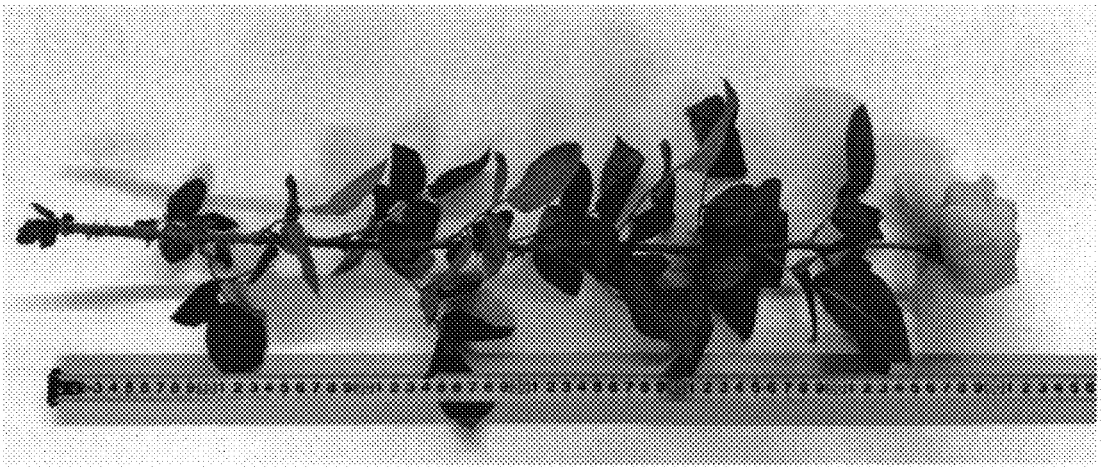
Figure 2:
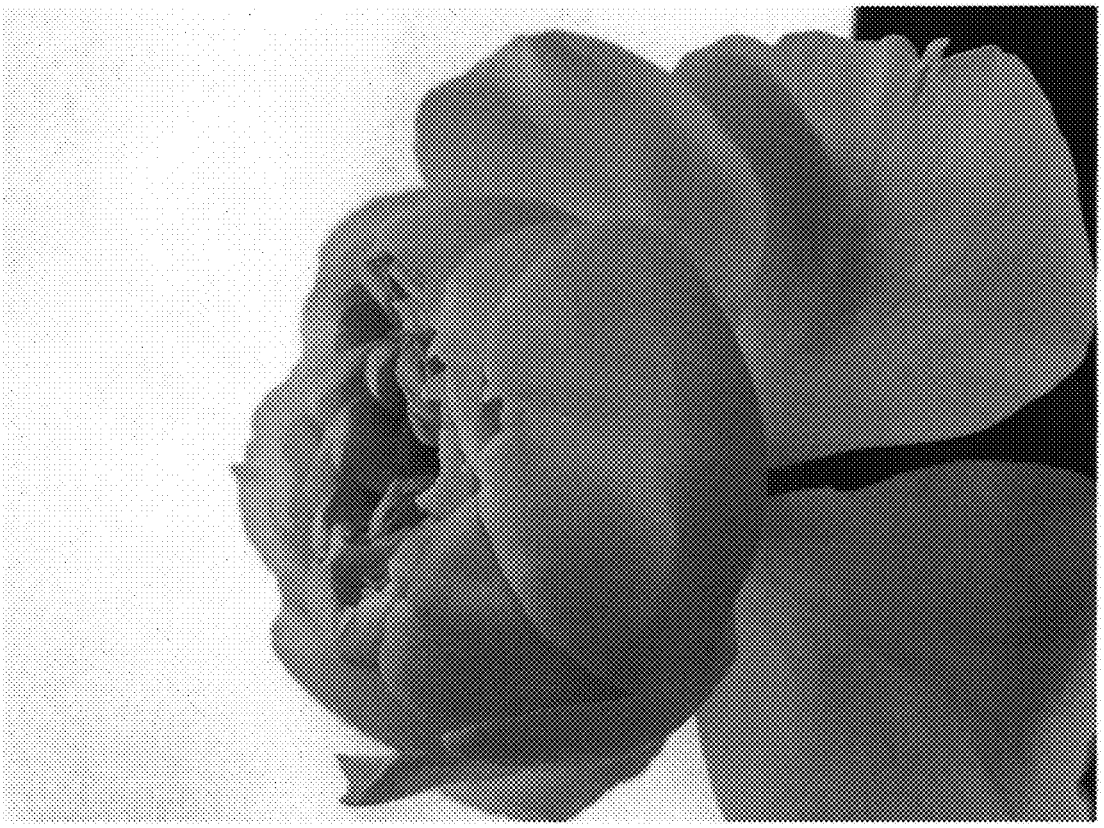
Figure 3:
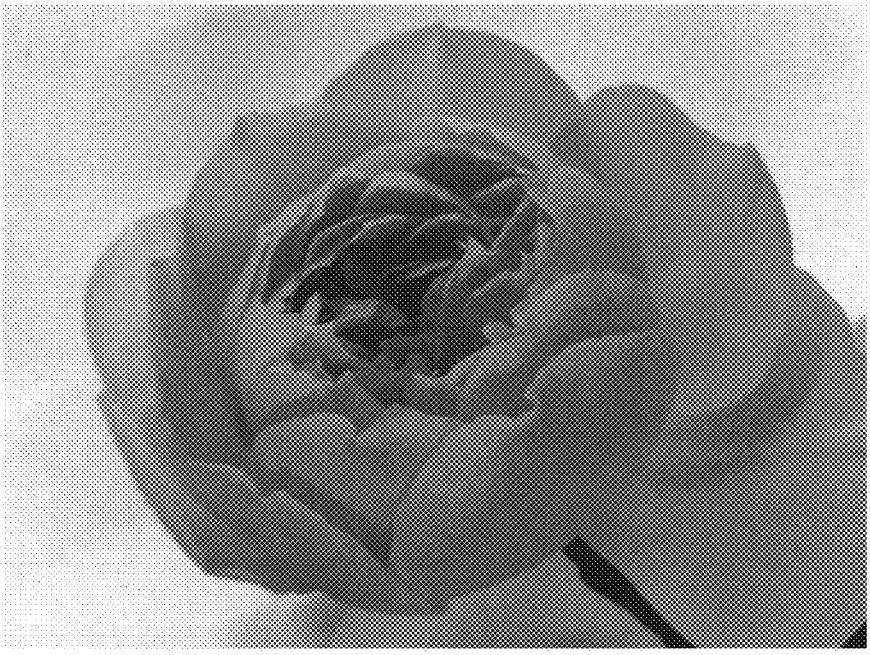
Figure 4:
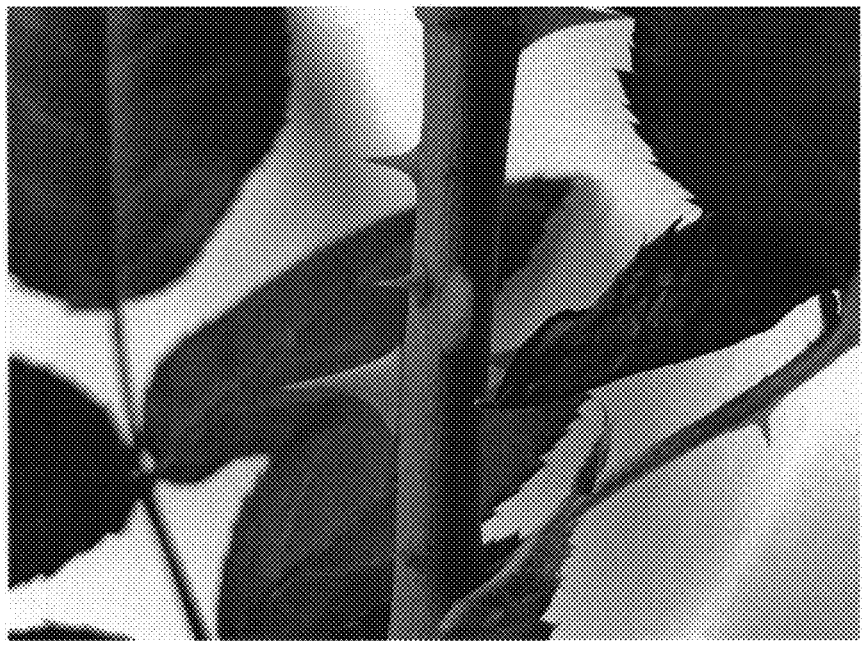
Figure 5:
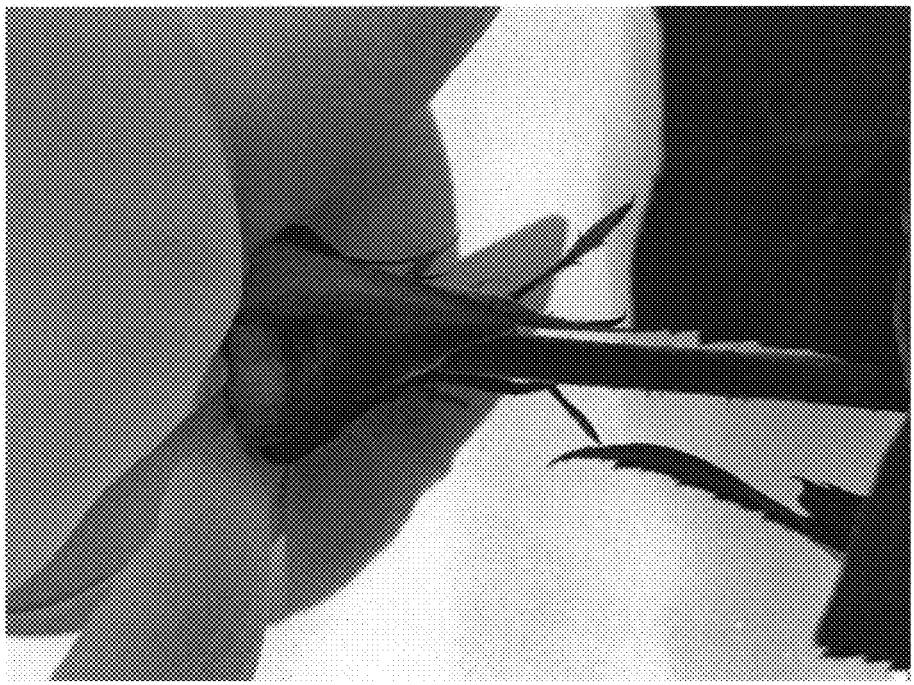
Figure 6:
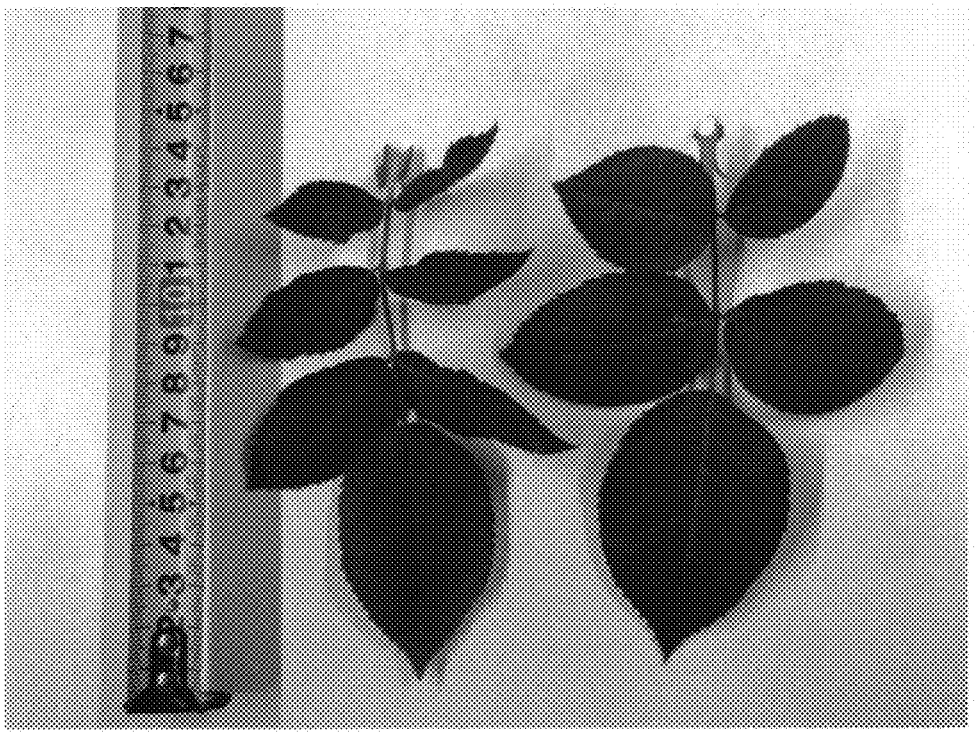
Figure 7:
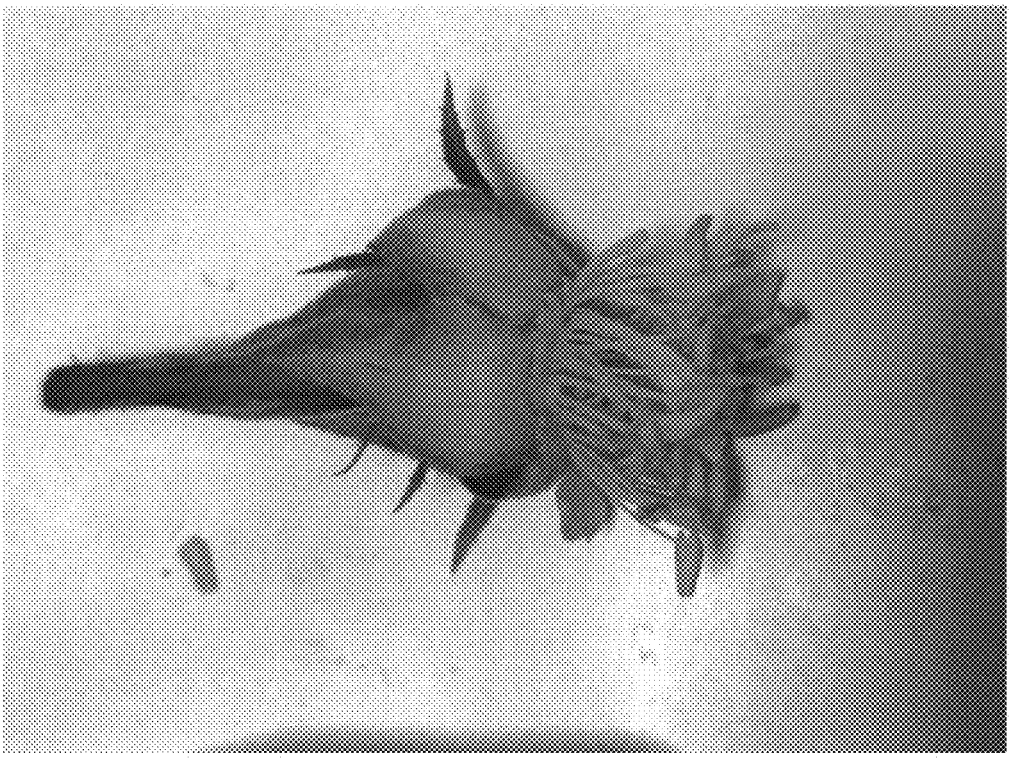
Figure 8:
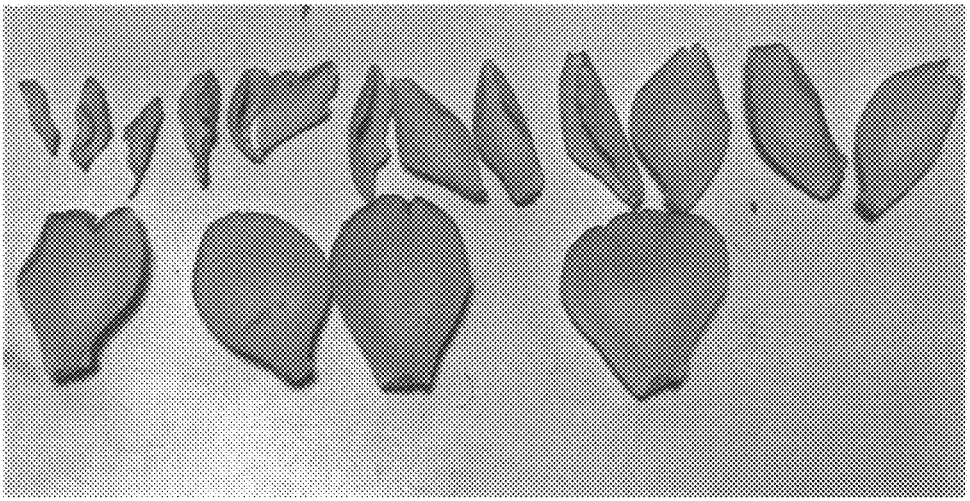

FIG. 1 shows a branch with a flower and leaves.
FIG. 2 shows a close-up side view of a flower.
FIG. 3 shows a close-up front view of a flower.
FIG. 4 shows the prickles on a branch.
FIG. 5 shows sepals at the base of a flower.
FIG. 6 shows leaves with leaflets.
FIG. 7 shows reproductive organs of a flower.
FIG. 8 shows individual petals.

DETAILED BOTANICAL DESCRIPTION

The following is a detailed description of '80100WABARA-CP' with color descriptions based on The Royal Horticultural Society (R.H.S.) Colour Chart published 2015 for those colors referred to by R.H.S. designation.

CHARACTERISTICS OF VARIETY

Plant:

*Growth type*.—Shrub.
*Growth habit*.—Semi-upright.
*Height*.—62 cm.
*Young shoot, anthocyanin coloration*.—Absent.
*Prickles, predominant color*.—146-C.

Leaf:

*Size*.—13.2 cm.
*Anthocyanin coloration*.—Absent.
*Glossiness of upper side*.—Very weak.
*Leaflet, undulation of margin*.—Very weak.
*Terminal leaflet, blade shape*.—Medium elliptic.
*Terminal leaflet shape of base of blade*.—Rounded.
*Terminal leaflet shape of apex of blade*.—Acuminate.

Flowers:

*Flowering shoot, flowering laterals*.—Present.
*Flowering shoot, number of flowering laterals*.—1 lateral.
*Flowering shoot, number of flowers*.—1 flower.
*Flowering shoot number of flowers per lateral*.—1 flower.
*Flower type*.—Double.
*Number of petals*.—80.
*Flower color*.—161-D.
*Density of petals (for double flowered variety)*.—Dense (on a scale of very loose, loose, medium, or dense).
*Flower diameter*.—9 cm.
*Flower shape*.—Rounded.
*Profile of upper part of flower*.—Flattened convex.
*Profile of lower part of flower*.—Flattened convex.
*Fragrance*.—Slightly like tea.
*Reflexing of petals one-by-one*.—Absent.
*Petal shape*.—Elliptic (center part), obcordate (outside).
*Petal incisions*.—Very weak.
*Reflexing of petal margin*.—Very weak.
*Petal undulation*.—Weak.
*Petal length*.—5.2 cm.
*Petal width*.—4.7 cm.
*Number of colors on inner side of petal*.—Two.
*Main color on inner side of petal*.—8D.
*Secondary color of petal*.—4C.
*Distribution of secondary color on inner side of petal*.—At base.
*Basal spot on the inner side of petal*.—Present.
*Size of basal spot on inner side*.—0.8-0.9 cm.
*Color of petal of basal spot on inner side of petal*.—7-A.
*Main color of petal on the outer side*.—11C.
*Outer stamen, predominant color of filament*.—15-C.
*Sepal, length*.—2-2.5 cm.
*Sepal, width*.—0.6-0.7 cm.
*Sepal, texture*.—Normal.
*Sepal, color*.—144-C.
*Sepal, shape*.—Weak extensions.
*Flower bud, length*.—1.5 to 2.5 cm.
*Flower bud, diameter*.—1 to 2 cm.
*Flower bud, shape*.—Sharp at the end.
*Flower bud, color*.—144-D.
*Receptacle, length*.—0.7 to 0.9 cm.
*Receptacle, width*.—0.6 to 0.9 cm.
*Receptacle texture*.—Normal.
*Receptacle color*.—144-A.
*Pedicel and peduncle, length*.—1.5 to 2 cm.
*Pedicel and peduncle, diameter*.—0.7 to 1 cm.
*Pedicel and peduncle texture*.—Normal.
*Pedicel and peduncle, color*.—29-C.
*Pollen color*.—15-A.
*Anthers, length*.—0.15 cm.
*Anthers, color*.—15-A.
*Anthers, quantity*.—20 to 30.
*Filament, length*.—0.4 to 0.6 cm.
*Pistil, length*.—0.4 to 0.6 cm.
*Stigma, color*.—17-D.
*Hips*.—Absent.
*Petiole, length*.—2 to 3 cm.
*Petiole, diameter*.—0.1 to 0.2 cm.
*Petiole, color*.—146-A.
*Rachies, length*.—6 to 7 cm.
*Color*.—146-B.
*Disease resistance/susceptibility*.—There is no specific disease or pest to which the plant is resistant or susceptible.

What is claimed is:

1. A new and distinct variety of a *Rosa* L. rose plant having the characteristics substantially as described and illustrated herein.

* * * * *